United States Patent [19]
Prendergast et al.

[11] Patent Number: 4,815,536
[45] Date of Patent: Mar. 28, 1989

[54] ANALYSIS OF MULTI-PHASE MIXTURES

[75] Inventors: Gavan J. J. Prendergast, Mount Waverley; David A. Webb, Northcote, both of Australia

[73] Assignee: Noel Carroll, Victoria, Australia

[21] Appl. No.: 945,662

[22] PCT Filed: Mar. 18, 1985

[86] PCT No.: PCT/AU86/00067
§ 371 Date: Jan. 16, 1987
§ 102(e) Date: Jan. 16, 1987

[87] PCT Pub. No.: WO86/05586
PCT Pub. Date: Sep. 25, 1986

[30] Foreign Application Priority Data

Mar. 19, 1985 [AU] Australia ............................ PG9815

[51] Int. Cl.⁴ ................... E21B 43/12; E21B 47/06; G01N 9/36; G01N 33/28
[52] U.S. Cl. ............................ 166/250; 166/53; 166/64; 166/66; 166/369; 166/372; 73/61.1 R
[58] Field of Search ............... 166/250, 369, 370, 372, 166/53, 64, 65.1, 66; 73/61.1 R, 155

[56] References Cited

U.S. PATENT DOCUMENTS

| | | | |
|---|---|---|---|
| 2,423,377 | 7/1947 | Ferguson, Jr. .................... | 73/23 X |
| 3,637,012 | 1/1972 | Sizer et al. ........................ | 166/250 |
| 3,906,198 | 9/1975 | November ................... | 73/61.1 R X |
| 3,910,110 | 10/1975 | Jefferies et al. ..................... | 73/155 |
| 3,981,183 | 9/1976 | Banks ............................. | 73/61.1 R |
| 4,059,744 | 11/1977 | Elderton ..................... | 73/61.1 R X |
| 4,201,082 | 5/1980 | Dockhorn et al. .................. | 73/153 |
| 4,429,581 | 2/1984 | Furmaga .......................... | 73/155 X |
| 4,441,362 | 4/1984 | Carlson ......................... | 73/61.1 R |
| 4,633,954 | 1/1987 | Dixon et al. ...................... | 166/53 X |

Primary Examiner—George A. Suchfield
Attorney, Agent, or Firm—Ladas & Parry

[57] ABSTRACT

A method for continuous analysis of mixtures for determining selective properties of components in the mixture flowing along a flow path includes the steps of, firstly, directly measuring and/or calculating the pressure, temperature, density and mass flow rate of the mixture at a first point upstream of a characteristic change zone in the flow path. A change in the characteristics of the mixture flow is caused in the characteristic change zone, and thereafter, the pressure, temperature, density and mass flow rate are measured directly and/or calculated at a second point downstream of a characteristic change zone. Selected properties of the mixture are determined on the basis of the information collected together with known parameters using algorithms.

17 Claims, 5 Drawing Sheets

ANALYSIS OF MULTI-PHASE MIXTURES

BACKGROUND AND FIELD OF THE INVENTION

This invention relates generally to a method and apparatus for determining selected properties of a multi-phase mixture.

Whilst it will be appreciated by those persons skilled in the art that the method and apparatus of the invention are readily applicable to the analysis of a wide variety of multi-phase mixtures, one particularly advantageous application relates to the analysis of the oil mixture discharged from an oil well. It will be convenient therefore to hereinafter describe the invention with reference to that particular application.

It is often necessary to be able to monitor and/or determine the various properties of the oil/gas/water mixture being discharged from an oil well. The properties of the mixture which are particularly important are the volume rate and density of each phase. It is the current practice when analysing the mixture discharged from an oil well to feed a relatively large quantity of the mixture to a "test separator". The "test separator" separates the multi-phase mixture into discrete phases before flow measurement is effected.

Separators of this general type are known and it is not proposed to provide a detailed description here. The major disadvantages of separators of this type are that they are relatively bulky and take up considerable space particularly when used on off-shore platforms. As a result each offshore platform usually has only one test separator, and this test separator is employed to take measurements from one well at a time. A further disadvantage is that they are relatively expensive.

It is an object of the present invention to provide a relatively simple method and apparatus for analysing multi-phase mixtures and with reference to the specific application referred to above, it is an object to alleviate one or more of the aforementioned disadvantages.

SUMMARY OF THE INVENTION

According to one aspect of the present invention there is provided a method of analysing multi-phase mixtures for determining selected properties of components in the mixture flowing along a flow path comprising the steps of directly measuring or calculating the density of the mixture at two or more points along the mixture flow path, directly measuring or calculating the mass flow rate of the mixture at at least one of the aforementioned points along said flow path and causing a change in the characteristics of the mixture flow between said one or more adjacent points and thereafter determining the selected properties on the basis of information collected.

The characteristic which is changed can be any one of a suitable group. For example the characteristic changed may be a pressure change or a temperature change or at least a partial separation of the phases in the mixture.

The characteristic change may also be effected by adding a substance to the mixture between the two points. This substance may be in the form of a chemical to cause a reaction or may be by the provision of a side stream of gas. In another arrangement, the characteristic change can be initiated by a change at some other point in the flow path which thereby causes the characteristic change. For example, a pressure differential upstream of the two points may be sufficient to cause a change between the points.

By using the above method, it is possible to determine the properties of the various phases of the mixture such as, for example, the volume and density of each particular phase. To determine these properties it may be necessary to carry out more than two density and/or mass flow measurements or calculations and where two or more measurements are carried out a corresponding flow characteristic changes are required between the adjacent measuring points. In some instances not all variables may be required to be determined purely from the mass flow measurement technique. For example, in mixtures such as the oil mixture from oil wells it may be convenient to assume that the density of the water phase and the oil phase remain constant along each pressure differential. From the information collected, it may be possible to produce suitable algorithms from which the required characteristics can be determined.

Thus in the particular example of a mixture discharged from an oil well, a series of equations can be written from which the various properties of the phases of the mixture can be determined.

In a typical example, it is reasonable to assume that the density of the oil and water remain substantially constant throughout the mixture flow. As such, it is possible to determine these values in any suitable manner. Using the method of the present invention the following properties are measured:

(a) The density of the mixture at points 1 and 2 ($\rho_1$ and $\rho_2$).

(b) The mass flow rate of the mixture ($M_{T1}$) (where the characteristic change is a pressure differential, the mass flow rate remains constant).

(c) The temperature and pressure at points 1 and 2.

(d) The density of the oil ($\rho_o$ and ) and water ($\rho_w$) (As mentioned earlier the density of the oil and water are measured separately).

$$P_1 = k_1 \rho_1 T_1 \tag{1}$$

$$P_2 = k_2 \rho_2 T_2 \tag{2}$$

$$M_{T1} = M_{T2} \tag{3}$$

$$M_{T1} = \rho_{g1}V_{g1} + \rho_{w1}V_{w1} + \rho_{o1}V_{o1} \tag{4}$$

$$M_{T2} = \rho_{g2}V_{g2} + \rho_{w2}V_{w2} + \rho_{o2}V_{o2} \tag{5}$$

$$V_{w1} = V_{w2} \tag{6}$$

$$V_{o1} = V_{o2} \tag{7}$$

$$V_{T1} = V_{g1} + V_{o1} + V_w \tag{8}$$

$$V_{T2} = V_{g2} + V_{o2} + V_{w2} \tag{9}$$

V is volume
subscript:
  g is gas
  o is oil
  w is water

If $\rho_{w1}$, $\rho_{o1}$, $\rho_{w2}$, $\rho_{o2}$, $k_1$, and $k_2$ are assumed or hand measured it is therefore possible to determine $V_{g1}$, $V_{g2}$, $\rho_{g1}$, $\rho_{g2}$, $V_{o1}$, $V_{o2}$, $V_{w1}$, $V_{w2}$, $V_{T1}$, $V_{t2}$.

According to another aspect of the present invention there is provided apparatus for analysing multi-phase mixtures comprising means for directly measuring the density of a mixture at at least two selected points along a flow path of the mixture, means for measuring the mass flow rate of the mixture at at least one of the points and means for using a change in the flow characteristics of the mixture between the points.

The apparatus of the present invention may comprise means for directly measuring the density of a mixture at at least two selected points along the path of travel of the mixture, means for measuring the mass flow rate of the mixture at at least one of the points and means for causing a change in the flow characteristics of the mixture between the points. It will be appreciated that this apparatus can be interfaced with a suitably programmed computer so that, for example, the properties of the mixture utilizing the equations above can be quickly determined.

The means for directly measuring the density and mass flow rate of the mixture may be in the form of a mass flow meter. A typical example of a suitable mass flow meter is sold under the trademark Micro Motion and is described in U.S. patent specification No. 422,338, now abandoned, and U.S. Pat. No. Re. 31,450. It may also be necessary to measure the temperature and pressure of the mixture at the mass flow meters and this can be done in any suitable manner. In another arrangement the density of the mixture could be measured by an on-line density meter one example of which is sold under the trademark SOLARTRON by the company Solartron Schlumberger.

If the characteristic change is a pressure differential then this can be caused by any suitable device such as a choke or the like.

If the characteristic change is a phase separation then in one preferred form a hydro cyclone of the type which is for example described in International application PCT/AU84/00195 which has been specifically developed for the treatment of oily water can be used. In one form the mass flow measurement may be taken at the inlet to the hydro cyclone and the outlet therefrom containing the oil/gas phase which is removed from the oil water mixture. In certain instances it may be necessary to use additional mass flow measurement meters with two or more hydro cyclones in series.

In the above described arrangements the mass flow measurement is of the total flow. It is possible however to merely take a sample of the flow and pass that sample through a device comprising two mass flow measurement meters with a pressure differential therebetween. Using such an arrangement however it is only possible to determine the relative percentage volumes of the phases.

BRIEF DESCRIPTION OF THE DRAWINGS

Preferred embodiments of the invention will hereinafter be described with reference to the accompanying drawings in which.

DETAILED DESCRIPTION OF THE PREFERRED EMOBODIMENTS

Figure 1:
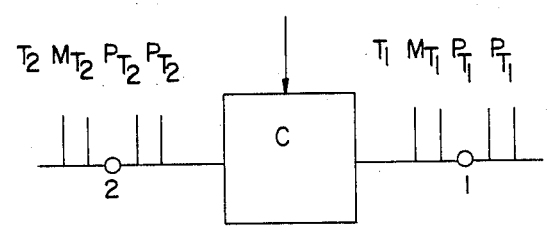
FIG. 1 is a schematic circuit drawing showing the general principle of the invention.

FIG. 1 shows schematically what may be required to be measured on-line at points 1 and 2 and with a characteristic change and C to determine the desired properties of the various phases in the mixture.

Figure 2:
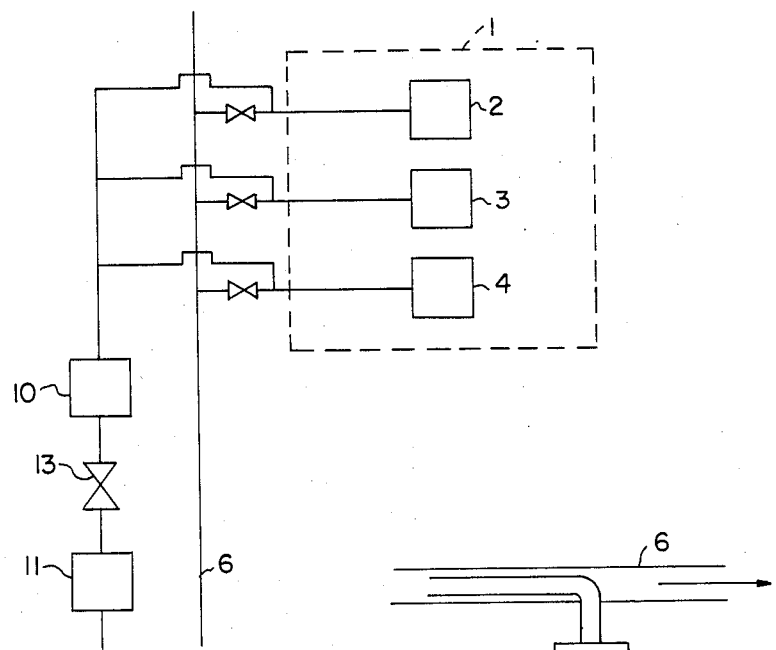
FIG. 2 is a schematic circuit drawing incorporating one form of device according to the invention.

Referring to FIG. 2 of the drawings, there is shown an oil rig 1 comprising oil wells 2, 3 and 4, a discharge line 6 for delivering the mixture to a separator (not shown). The device of the present invention comprises a pair of mass flow meters 10 and 11 having a choke 13 therebetween. The mass flow meters can measure the mass flow as well as the density of the mixture.

Figure 3:
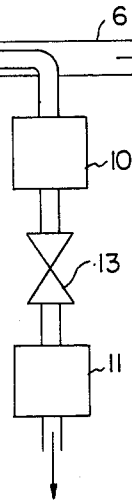
FIG. 3 shows an arrangement by which a sample of the mixture is taken from the main line.

In FIG. 3, there is shown an embodiment where a sample is taken from the main delivery line 6, the sample passing through mass flow meters 10 and 11 and choke 13.

Figure 4:
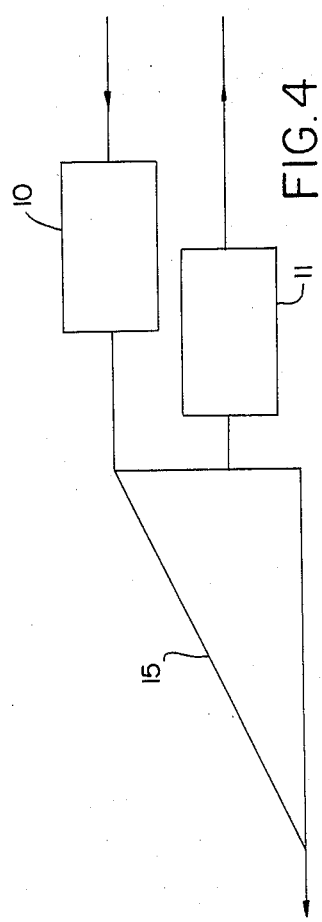
FIGS. 4 and 5 show a form of the apparatus when used with hydro cyclones.
Figure 5:
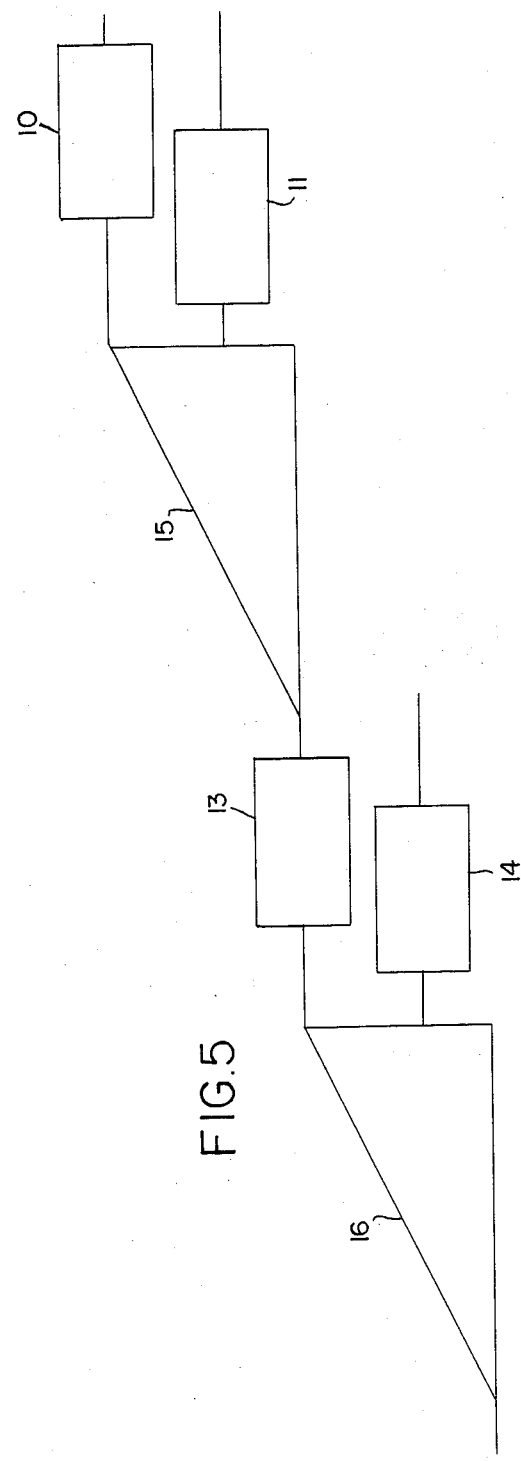

In FIGS. 4 and 5 there is shown the arrangement of mass flow meters 10, 11 13 and 14 with hydro cyclones 15 and 16. In this particular arrangement the characteristic change as effected by phase separation. For example, in FIG. 4 mass flow meter 10 measures the mass flow and density of the mixture in total and mass flow meter 11 measures the mass flow and density of the oil and gas phases. It is therefore possible to device equations to determine the desired properties of each phase.

One application of the invention relates to gas optimization of oil wells. To bring the oil water mixture to the surface of a well, gas is delivered down the well and thereby reduces the mass of the mass of the column of mixture within the production tubing. As a result of this mass reduction, the reservoir pressure causes the column to rise to the surface.

Figure 6:
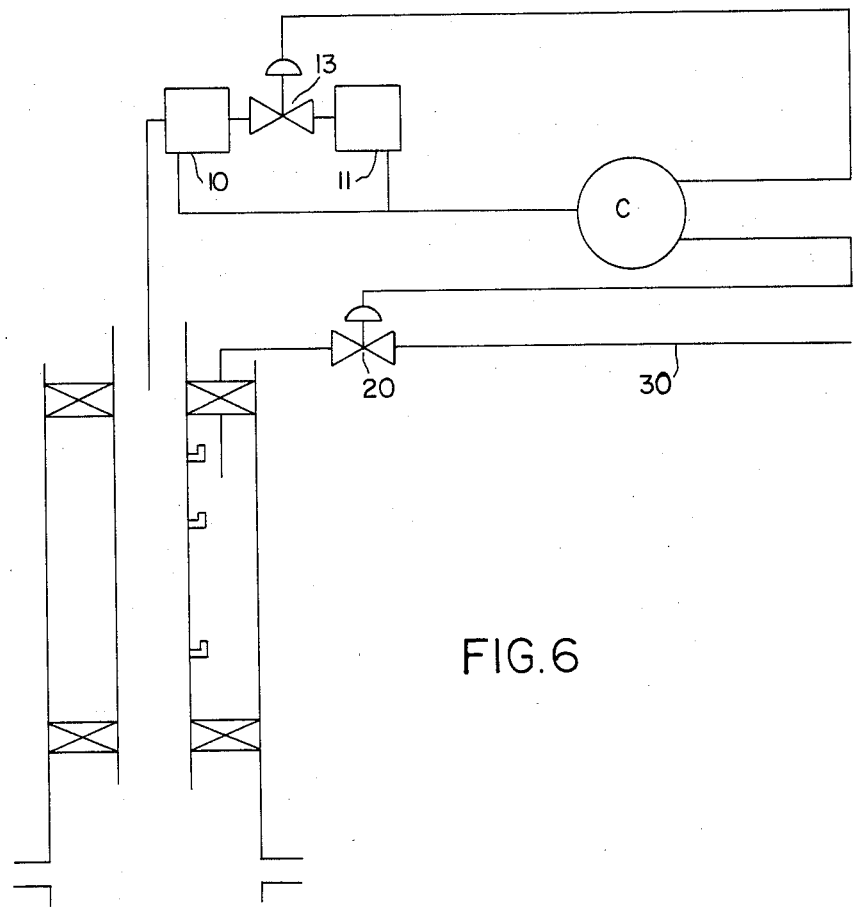
FIG. 6 is a circuit diagram showing a use of the apparatus in relation to gas optimization.

The amount of gas fed down the well will affect the oil/water/gas mixture delivered to the surface. Thus, by controlling the gas flow the desired oil/water/gas mixture can be controlled. FIG. 6 is one example of how the gas flow can be controlled using the method and apparatus of the presnet invention.

Gas is fed under pressure along line 30 through throttling valve 20 down the well where it mixes with the column of oil/water and sometimes gas to bring the mixture to the surface. The properties of the mixture are determined through mass flow meters 10 and 11 and choke valve 13 and the information fed to controller C. The controller then opens or closes throttling valve 20 as required.

Figure 7:
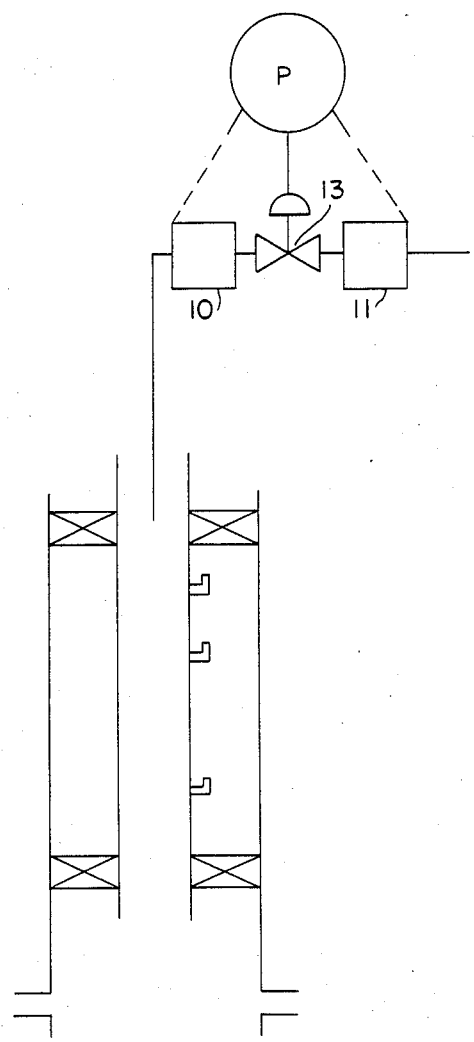
FIG. 7 is a circuit diagram showing a use of apparatus for controlling discharge from an oil well head.

In FIG. 7 there is shown an arrangement whereby well flow is controlled by the control of the well head choke. In this installation, two mass flow meters 10 and 11 are operatively connected to the well output line, the meters being disposed on opposite sides of the choke 13. The instrumentation provided at each point consists of a temperature transmitter, a pressure transmitter and a density transmitter.

The transmitter measurements are adapted to be fed to a processor P such as a computer containing data and algorithms regarding characterization of gas pressure/temperature/volume/density relationships, mass balance relationships and data regarding oil and water properties as a function of temperature and pressure. The processor P uses this data and the transmitter signals to determine oil, water and gas mass and volumetric flow rates. This information is used as a basis for controlling the position of the choke. This may be done automatically or manually.

By employing the multi-phase analysis system of the invention, for example, on an off-shore platform with multiple wells, continuous measurement of production from each well can be achieved. This can lead to improved reservoir management. The analysis also provides for a more representative flow measurement from the well head due to an improved response time compared to the "test separator" discussed earlier.

In the particular example given above, the system is likely to be able to monitor slugging flow whereas the "test separator" cannot effectively owing to its poor response time.

An example of multi-phase measurement according to the present invention is given below for measurement of a distillate fuel oil/water/air mixture, the measurement being done in a laboratory.

Figure 8:
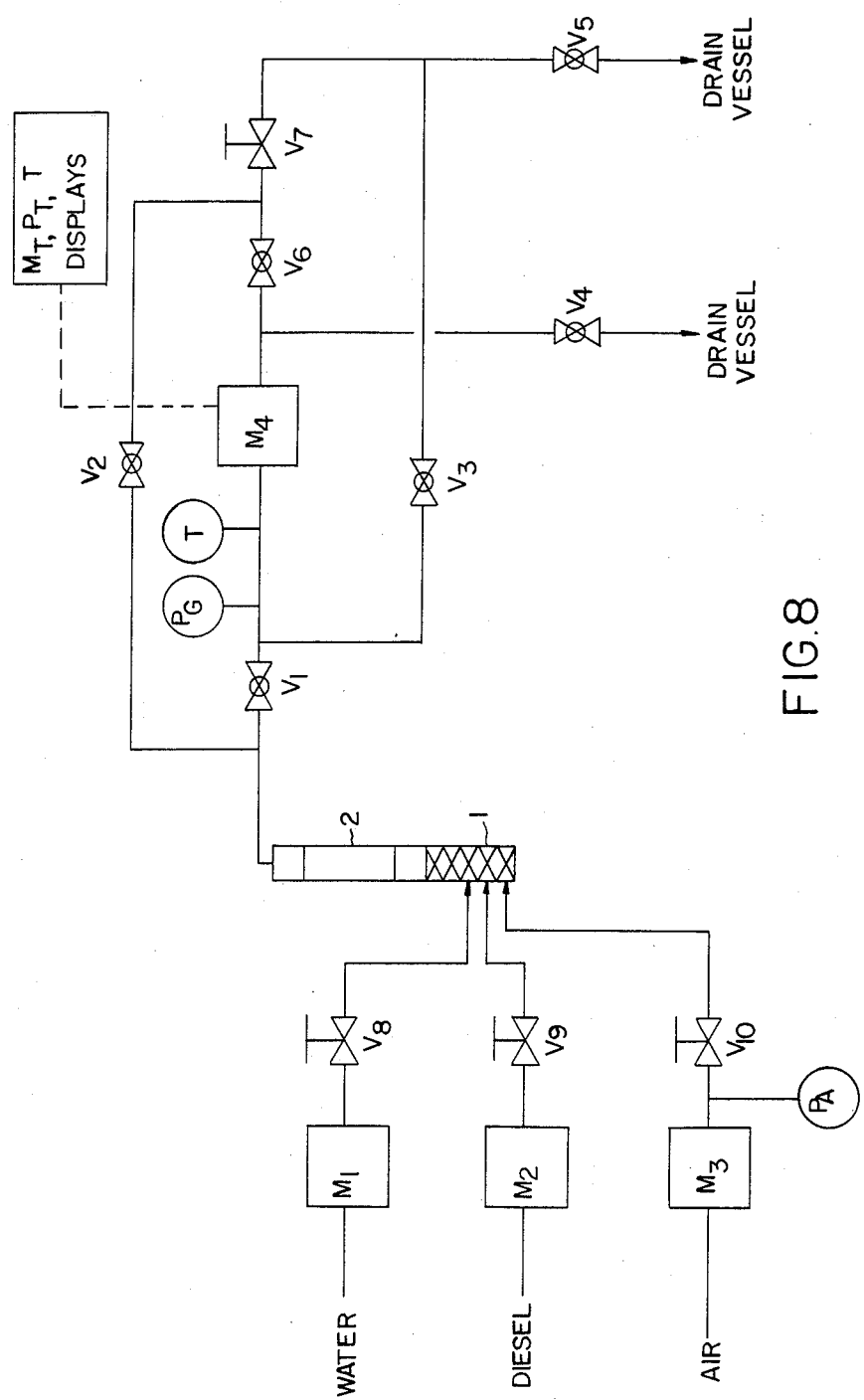
FIG. 8 is a circuit diagram of apparatus used in the example.

FIG. 8 shows the layout of the test installation. The mixture tested was a mixture of diesel, water and air. The water, diesel and air were fed into the system via flow meters $M_1$, $M_2$ and $M_3$ and through gate valves $V_8$, $V_9$ and $V_{10}$ respectively. $M_1$ was a Fisher and Porter Rotameter $M_2$ a VAF positive displacement vane meter and $M_3$ a Fisher and Porter Purge Rotameter. The gate valves were used to vary the inlet flows.

The flow of the various phases passed to a static flow mixer 1 which provided for a homogeneous three phase flow. A clear pipe section 2 was provided for enabling visual inspection.

The mixture passed to the test circuit section of the installation where measurement of the flow rate was made by meter $M_4$ which was a Micrometer D40 mass flow meter with the DT7 density and temperature and DT10 flow rate and flow stabilization units. The flow meters $M_1$, $M_2$ and $M_3$ were calibrated against meter $M_4$ before the test and the meter $M_4$ was volumetrically calibrated before the test.

The pressure gauge $\rho g$ measured the pressure at the meter $M_4$ and the pressure gauge $\rho a$ was used in conjunction with meter $M_3$ to give the inlet air flow.

The valves $V_1$, $V_2$, $V_3$, $V_4$, $V_5$ and $V_6$ were arranged to control the direction of flow and $V_7$ was the pressure dropping gate valve. This valving arrangement was used to simulate upstream and downstream of the pressure dropping valve $V_7$. As such, it was only necessary to use one meter $M_4$ rather than two.

Initial readings were taken of the three inlet flows and upstream conditions at the meter $M_4$ thereafter the system was reversed to simulate downstream conditions and further readings were taken. Table 1 sets out the results of four tests conducted.

The mathematics involved with test number 2 are given below.

Initial Known Data

Density of water ($\rho w$): 1.00 s.g.
Density of diesel ($\rho d$): 0.828 s.g.
Density of air ($\rho g$): $1.29 \times 10^{-3}$ (0° C. 1 Atmos)

| | Before Valve $V_7$ (UPSTREAM) | | After Valve $V_7$ (DOWNSTREAM) | |
|---|---|---|---|---|
| $M_{T1}$ | 19.2 | Kg/min | $M_{T2}$ | 19.2 |
| $P_1$ | 330 | KPng | $P_2$ | 265. |
| $T_1$ | 19.4 | °C. | $T_2$ | 19.4 |
| $\rho_{T1}$ | .825 | s.g. | $\rho_{T2}$ | .812 |

Inlet Conditions $V_d'$ 10.7 l/min: $V_w'$ 10.4 l/min: $V_g'$ 2.2 l/min

The above flows were corrected to calibrated flows from original readings.

Calculating volume flows from above $$V_{T1} = \frac{M_{T1}}{\rho_{T1}} \qquad V_{T2} = \frac{M_{T2}}{\rho_{T2}}$$
$$= 23.2 \text{ l/min} \qquad = 23.6 \text{ l/min}$$

$\Delta V_T = V_{T2} - V_{T1} = 0.4$ l/min
$V_{T1} = V_d' + V_w' + V_g' = 23.3$ l/min The expected change in $V_T$ due to the change in gas volume induced across $V_T$ can be calculated from PV=n RT (ideal gas).

For this case n RT is constant.

$$\therefore V_{g2} = \frac{P_1}{P_2} \cdot V_{g1} \text{ (using } V_g' =$$
$$V_{g1} = 1.7 \text{ l/min @ 470 } KPng)$$
$$\Delta V_g = 2.2 \text{ l/min } V_{g2} = 2.6 \text{ l/min}$$
$$V_{g2} - V_{g1} = 0.4 \text{ l/min}$$

(This reuult compares with $\Delta V_T$ as measured by $M_4$ of 0.4 l/min).

Given that the volume flow rates of diesel and water will remain constant across $V_7$; that is $$V_{d1} + V_{w1} = V_{d2} + V_{w2}$$

then the measured change in volume flow rate across $V_7$ is the flow rate change in the gas phase; that is $$V_{T2} - V_{T1} = V_{g2} + V_{d2} + V_{w2} - V_{g1} + V_{d1} - V_{w1}$$
$$= V_{g2} - V_{g1}$$
$$= \Delta V_g = 0.4 \text{ l/min}$$

Using the ideal gas law in this instance $$V_{g2} = V_{g1} + \Delta V_g$$
$$= n\frac{RT_1}{P_1} + \Delta V_g = \frac{nRT_2}{P_2}$$
$$nR = \frac{\Delta V_g}{\frac{T_2}{P_2} - \frac{T_1}{P_1}}$$

From the above result
$\Delta V_g = 0.4$ l/min
$T_1 = T_2 = 19.4°$ C.
$P_1 = 330$ KPag
$P_2 = 265$ KPag
$nR = 3.3$
At meter $M_3$ $Pa = 470$ KPag $T = 20°$ C.

$$V_g = \frac{3.3 \times 293}{571} = 1.7 \text{ l/min}$$

This compares with the calibrated inlet volume of 1.7 l/min. Changing the above flow rate to the flow rates at the upstream and downstream
$V_{g1} = 2.2$ l/min
$V_{g2} = 2.6$ l/min To find the gas density at the above conditions it is necessary to know its molecular weight $M = 29$ kg/kmol $\rho_{g1} = 5.1$ g/l $\rho_{g2} = 4.3$ g/l The calculation of the water and diesel flow rates can be found from the following equations $$V_w = \frac{M_{T1} - M_{g1} + \rho_d(V_{g1} - V_{T1})}{\rho_w - \rho_d}$$

$$V_d = \frac{M_{T1} - M_{g1} + \rho_w(V_{g1} - V_{T1})}{\rho_d - \rho_w}$$

Substituting values into the above $V_w = 10.5$ $V_d = 10.5$

These are comparable to the inlet flows.

TABLE 1

| | BEFORE VALVE (UPSTREAM) | | | | | AFTER VALVE (DOWNSTREAM) | | | | | INLET CONDITIONS | | | | |
|---|---|---|---|---|---|---|---|---|---|---|---|---|---|---|---|
| | $M_{T1}$ kg/min | $P_1$ kPag | $T_1$ °C. | Density $\rho_{T1}$ | $V_{T1}$ | $M_{T2}$ | $P_2$ | $T_2$ | Density $\rho_{T2}$ | $V_{T2}$ | Diesel $V_d'$ | Water $V_w'$ | Air $V_g'$ | $V_{T1}'$ | $M_{T1} \sim \rho_d V_d' + \rho_w V_w'$ |
| (1) | 19.0 | 325 | 19.5 | .873 | 21.8 | 19.0 | 260 | 19.4 | .863 | 22.0 | 10.8 | 9.9 | .91 | 21.6 | ~18.7 |
| (2) | 19.2 | 330 | | .825 | 23.2 | 19.2 | 265 | | .812 | 23.6 | 10.7 | 10.4 | 1.72 | 22.8 | ~19.3 |
| (3) | 19.0 | 360 | | .775 | 24.3 | 19.0 | 295 | | .759 | 25.1 | 10.8 | 9.8 | 3.7 | 24.4 | ~18.7 |
| (4) | 17.4 | 325 | | .751 | 23.2 | 17.4 | 215 | | .719 | 24.3 | 14.5 | 5.2 | 3.4 | 23.1 | ~17.2 |
| | | | | $V_T = \frac{M_T}{\rho_T}$ | | | | $\Delta V_T = V_{T2} - V_{T1}$ | | | $\Delta v_g = V'_{g1} - V_{g2}$, $V_{g1,2}$ calculated from gas law and pressures at measurement points. | | | | |
| (1) | | | | | | | | 0.2 | | 0.2 | | | | | |
| (2) | | | | | | | | 0.4 | | 0.4 | | | | | |
| (3) | | | | | | | | 0.6 | | 0.6 | | | | | |
| (4) | | | | | | | | 1.1 | | 1.2 | | | | | |

We claim:

1. A method for continuous analysis of mixtures for determining selective properties of components in the mixture flowing along a flow path, the method including the steps of:
   (a) Firstly, directly measuring and/or calculating the pressure, temperature, density and mass flow rate of the mixture at a first point upstream of a characteristic change zone in the flow path;
   (b) causing a change in the characterisitcs of the mixture flow in said characteristic change zone;
   (c) thereafter measuring directly and/or calculating the pressure, temperature, density and mass flow rate at a second point downstream of said characteristic change zone; and
   (d) determining the selective properties of the mixture on the basis of the information collected together with known parameters using algorithms.

2. A method according to claim 1 wherein the characteristic which is changed is a pressure change.

3. A method according to claim 1 wherein the characteristic which is changed is a temperature change.

4. A method according to claim 1 wherein the characteristic which is changed is at least a partial separation of the phases in the mixture.

5. A method according to claim 1 wherein said characteristic change is initiated by a change other than between said two points which causes said characteristic change.

6. A method according to claim 1 including the step of utilizing an interfaced computer to determine the selected properties.

7. Apparatus for continuous analysis of mixtures for determining selective properties of components in the mixture flowing along a flow path, the apparatus comprising:
   a first mass flow meter for directly measuring the density and mass flow rate at a first point upstream of a characteristic change zone in the flow path;
   means for causing a change in the characterisitcs of the mixture flowing in said characteristic change zone; and
   a second mass flow meter for directly measuring the density and the mass flow rate of the mixture at a second point downstream of the characteristic change zone, the arrangement being such that selected properties of the mixture can be determined on the basis of the information collected together with known parameters using algorithms.

8. Apparatus according to claim 7 including a computer arranged so that the properties of the mixture can be determined from the information obtained from the other parts the apparatus.

9. Apparatus according to claim 8 wherein said means for directly measuring the density and mass flow rate of the mixture is in the form of a mass flow meter (10, 11).

10. Apparatus according to claim 7 wherein said means for directly measuring the density and mass flow rate of the mixture is in the form of a mass flow meter (10, 11).

11. Apparatus according to claim 7, wherein the characteristic changed is a pressure differential caused by a choke valve (13).

12. Apparatus according to claim 7 wherein the characteristic changed is a phase separation by a hydro cyclone (15, 16).

13. A method of controlling discharge from a well head comprising the steps of analysing the multi-phase mixture being discharged from the well head in accordance with claim 1 and from the results obtained controlling the discharge conditions in a selected manner.

14. A method according to claim 13 wherein the discharge of the mixture from the well is controlled by a choke, the method including operating the choke in response to the results obtained.

15. A method according to claim 13 wherein the discharge of the mixture from the well is controlled by the delivery of gas to the well the method including controlling the delivery of the gas in response to the results obtained.

16. Apparatus for controlling discharge from a well head the apparatus being characterized by multi-phase analysis apparatus for analysing multi-phase mixtures according to claim 7 a choke (13) operatively connected to the discharge line from the well head and control means (P) for controlling opening and closing of said choke said control means being operable in response to information received from said multi-phase analysis apparatus.

17. Apparatus for controlling discharge from a well head, the apparatus being characterized by multi-phase analysis apparatus according to claim 7 means (30) for delivering gas to the well having valve means (20) controlling the quantity of gas delivered and control means (C) for controlling opening or closing of said valve means said control means being operable in response to information received from said multi-phase analysis apparatus.

* * * * *